Figure 1:
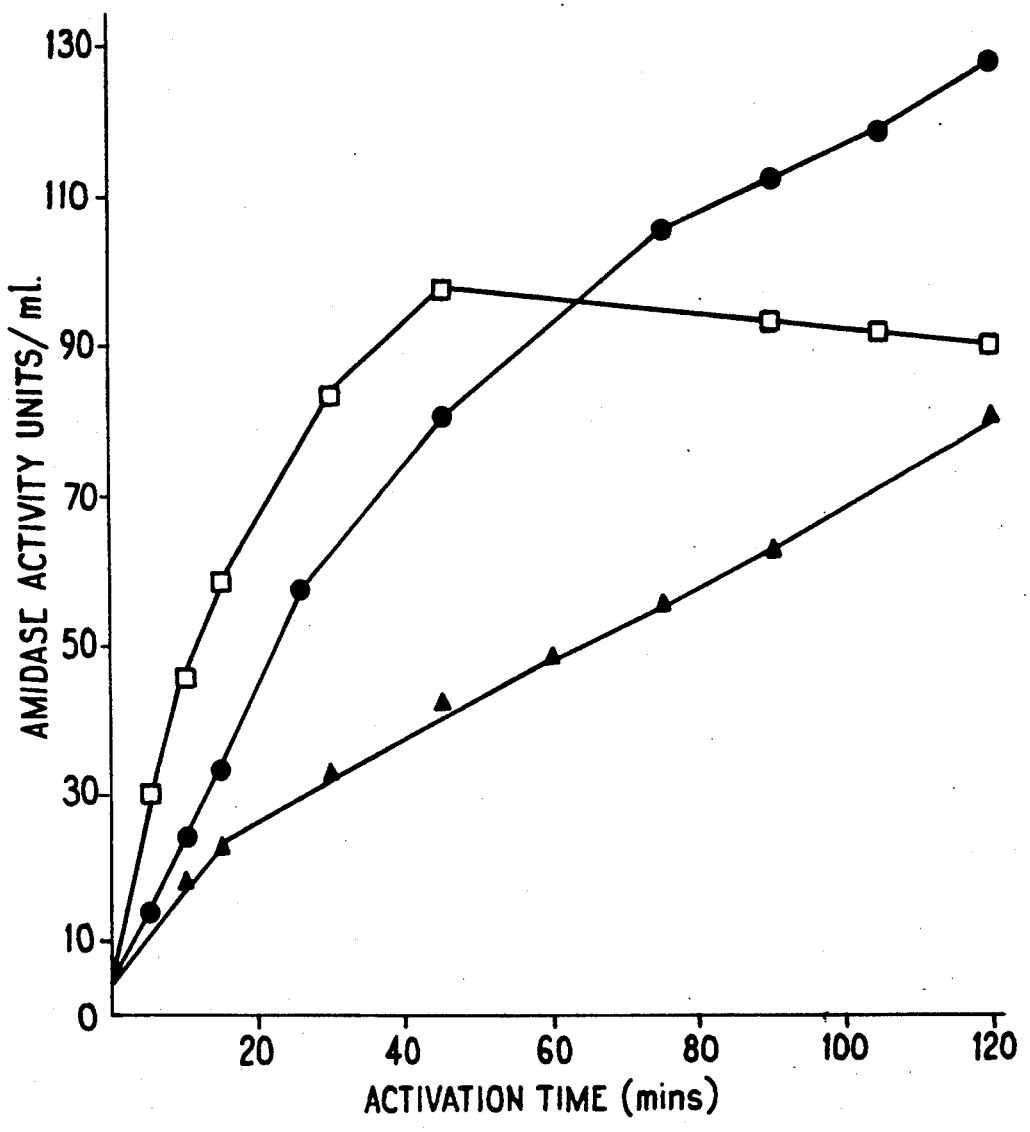

United States Patent [19]

Carver et al.

[11] Patent Number: 5,188,952
[45] Date of Patent: Feb. 23, 1993

[54] PROCESS FOR THE DECOMPOSITION OF ACRYLAMIDE

[75] Inventors: Mark A. Carver, Stockton-on-Tees; John Hinton, Middlesbrough, both of United Kingdom

[73] Assignee: Imperial Chemical Industries PLC, London, England

[21] Appl. No.: 647,696

[22] Filed: Jan. 29, 1991

Related U.S. Application Data

[63] Continuation of Ser. No. 133,285, Dec. 14, 1987.

[30] Foreign Application Priority Data

Dec. 16, 1986 [GB] United Kingdom ............... 8630012

[51] Int. Cl.$^5$ .................... C12P 7/42; C12N 9/80; C12S 13/00
[52] U.S. Cl. ................................ 435/146; 435/228; 435/262
[58] Field of Search ............... 435/228, 262, 146, 816

[56] References Cited

U.S. PATENT DOCUMENTS

| | | | |
|---|---|---|---|
| 4,425,797 | 5/1990 | Byrom et al. | 435/135 |
| 4,532,214 | 7/1985 | Szajani et al. | 435/228 |
| 4,687,807 | 8/1987 | Wetegrove et al. | 524/827 |

FOREIGN PATENT DOCUMENTS

| | | |
|---|---|---|
| 0272025 | 6/1988 | European Pat. Off. . |
| 55-42534 | 7/1980 | Japan . |
| 1158580 | 1/1985 | U.S.S.R. . |

OTHER PUBLICATIONS

Chemical Abstracts, vol. 91, No. 11, No. 89550d.
Asano et al, Agric. Biol. Chem., 45(5):1175–1181, (1982).
Chem. Abs. 91, 112077v (1979)–Jap. Pat. Publn.; 7911389 to Taki Chem Co.
Chem. Abs. 91, 89550d, (1979)–Jap. Kokai 7941392 to Mitsubishi.
J. Basic Microbiol., 26, 5, 299–311, (1986).

Primary Examiner—Charles L. Patterson, Jr.
Attorney, Agent, or Firm—Cushman, Darby & Cushman

[57] ABSTRACT

A process for the decomposition of acrylamide using an amidase (acrylamide amido hydrolyase) enzyme in which the enzyme has been heated to a temperature in the range 40° to 80° to induce increased activity of the enzyme. A method for preparing the enzyme and a process for producing acrylic acid are also claimed. The process for the decomposition of acrylamide is useful in particular for reducing the level of unreacted monomer associated with homo- and hetero-polymers of acrylamide. A temperature in the range 50° to 62° is particularly preferred for heating.

6 Claims, 5 Drawing Sheets

AMIDASE. HEAT ACTIVATION

AMIDASE. REMOVAL OF ACRYLAMIDE FROM AN ANIONIC LATEX TYPE A626

ANIONIC LATEX. NALFLOC TYPE A626
ENZYME LOADING 1000 U/Kg
TEMPERATURE 60°C
pH 5.9

REMOVAL OF FREE ACRYLAMIDE FROM A NONIONIC LATEX NALFLOC TYPE 8861-SC.

TEMPERATURE 60°C
pH 6.0
ENZYME LOADING 1000 U/Kg LATEX.

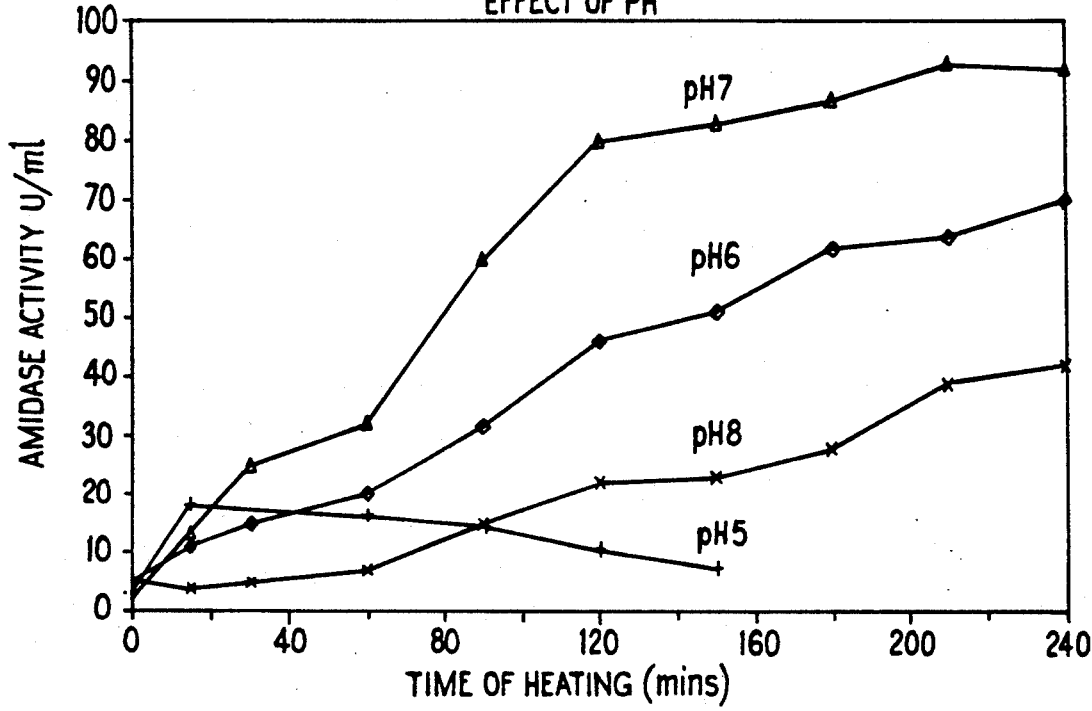
FIG.5 AMIDASE HEAT ACTIVATION EFFECT OF PH
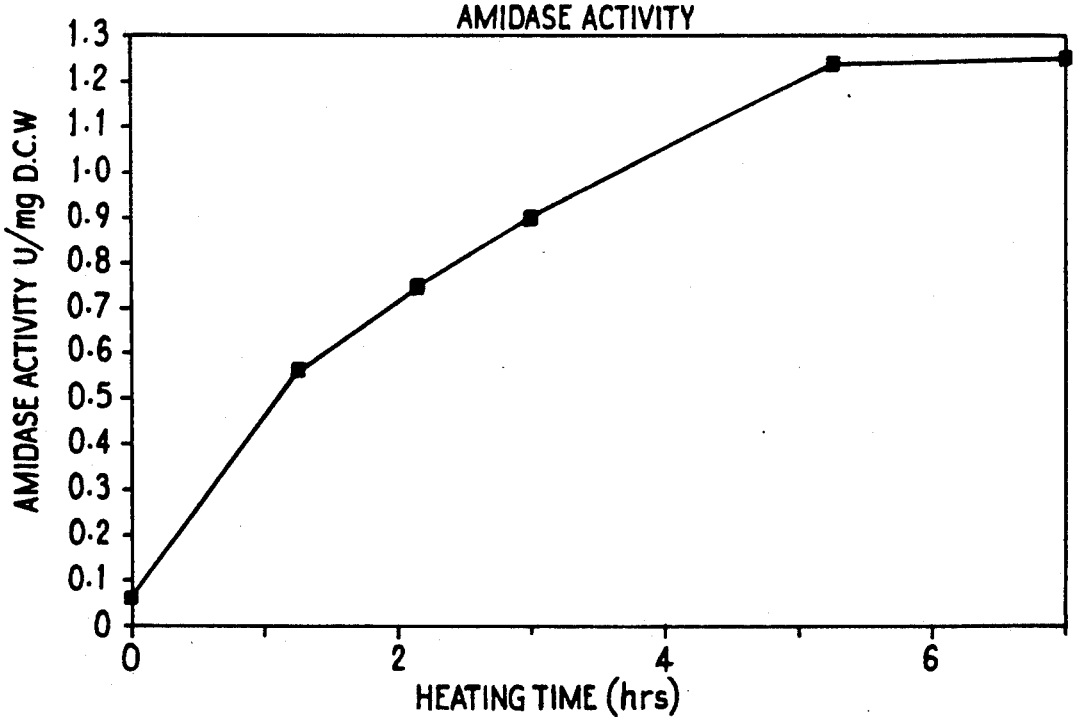
FIG.6 HEAT TREATMENT OF CELL PASTE AMIDASE ACTIVITY

PROCESS FOR THE DECOMPOSITION OF ACRYLAMIDE

This is a continuation of application Ser. No. 07/133,285, filed on Dec. 14, 1987.

This invention relates to a process for the decomposition of acrylamide, to a method for the production of the enzyme amidase (acylamide amidohydrolase EC No. 3-5-1-4) used in the decomposition of acrylamide and to a process for the production of acrylic acid or a salt or ester thereof by decomposition of acrylamide.

Polyacrylamide polymers, i.e. homo- and heteropolymers of acrylamide, are widely used as flocculants in the potable water industry, sewage treatment, paper manufacture and mining. However their utility is restricted and they cannot for instance be used in connection with foodstuffs because they are generally contaminated with unreacted acrylamide monomer which is a cumulative neurotoxin and a carcinogen. At present polyacrylamides are generally allowed in the U.S.A. to contain up to 500 ppm of unreacted acrylamide and this limit is likely to be introduced elsewhere. This level of unreacted monomer can be achieved by use of longer polymerisation times and by a "heat treating" process. Such treatments increase cost of manufacture and reduce the efficiency of the polymers produced by causing branching in these polymers. Linear polymers have a higher flocculation efficiency and are preferred. There is a need for a reliable process for reducing the level of unreacted monomer in polyacrylamides without damage to the polymer to 500 ppm and preferably to even lower levels (5–10 ppm or lower). If the unreacted monomer present could be reduced reliably to very low levels (1–5 ppm or less) polyacrylamides could be considered for uses from which they are presently excluded, e.g. in the manufacture of food contact materials or in direct contact with food.

Japanese Patent Publication No. 79011389 (corresponding to Japanese kokai No. 53086078) discloses a process for the decomposition of acrylamide monomer, e.g. in waste water or in polyacrylamides by contacting with an intracellular enzyme of *Brevibacterium ammoniogenes* preferably of strains ATCC 1641, ATCC 6871 and ATCC 6872. However, despite being known for a number of years, this process does not appear to have been used commercially to any significant extent. Moreover *Brevibacterium ammoniogenes* enzyme works poorly in polyacrylamide latex systems.

It is desirable that amidase enzymes having increased activity should become readily available commercially.

According to the present invention we provide a method for the production of an amidase enzyme of increased activity wherein microbial cells or extracts containing the enzyme are heated to a temperature in the range 40° to 80° C. for a sufficient period and under such conditions that a significant increase in amidase activity is induced. Microbial cells and extracts having increased amidase activity produced by the method of the invention are also included in the scope of the invention.

Further according to the invention we provide a process for the decomposition of acrylamide in a medium containing it in which the medium is contacted with an enzyme capable of decomposing acrylamide under conditions suitable for the enzyme to decompose the acrylamide wherein the enzyme is an amidase enzyme which has been heated to a temperature in the range 40° to 80° C. for a sufficient period under suitable conditions to increase the activity of the enzyme.

Further according to the invention we provide a process for the production of acrylic acid or a salt or ester thereof in which a medium containing acrylamide is contacted with an enzyme capable of decomposing acrylamide to acrylic acid under conditions suitable for the enzyme to decompose the acrylamide to acrylic acid or a salt or ester thereof wherein the enzyme is an amidase enzyme which has been heated to a temperature in the range 40° to 80° C. for a sufficient period under suitable conditions to increase the activity of the enzyme.

Amidases are part of the nitrogen assimilation apparatus of many cells grown under conditions where the sole source of nitrogen is an aliphatic amide.

Thus the metabolic role of amidase is to release ammonia from said amide, e.g. by the following reaction:

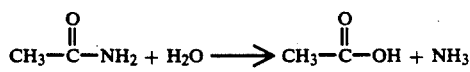

The ammonia released is then assimilated into protein biosynthesis. The aliphatic acid produced may or may not be assimilated dependent upon the microorganism type.

Amidases can also catalyse the conversion of acrylamide to acrylic acid by the following reaction:

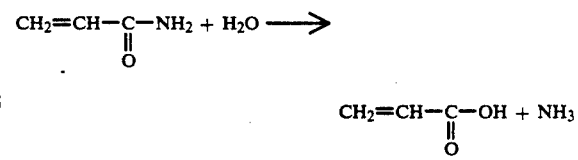

In the presence of appropriate salts or alcohols the acrylic acid produced can be converted to its salt or ester.

The decomposition process of the invention can be used to decompose acrylamide in any medium in which it occurs. It is particularly useful for decomposing unreacted acrylamide present in polyacrylamide polymers and acrylamide present in waste waters, e.g. waste water from a process for the production of polyacrylamides. Polyacrylamides are produced as polymers of three types i.e. solution, dry and suspension polymers.

Polyacrylamides are produced as polymers of three chemical types. These are cationic, anionic and nonionic polymers wherein acrylamides may be copolymerised with other monomers, e.g. acrylic acid. These polymers may be manufactured by one of the following three basic technologies:

Solution polymerisation wherein monomers are polymerised in aqueous solution to produce a gel-type product;

Dry polymers which are polymers produced as above but which are subsequently heat dehydrated prior to use;

Latex or suspension polymerisation wherein a solution of monomers in water is admixed with detergents and a non-aqueous low odour paraffinic solvent to form a stable suspension of aqueous droplets within which beads of polymers are formed by addition of a water soluble polymerisation initiator to the system.

Latex or suspension polymers form the largest group of polyacrylamides in terms of market share.

The amidase enzyme used in the decomposition and acrylic acid production processes of the invention may be present in any suitable form in whole microorganism cells or as a crude or purified enzyme extract. The enzyme can be introduced to the processes in whole cells in the culture produced initially in the method of the invention or in a medium produced after only partial separation of water and other components from such a culture. Generally however it is preferred that the cells should be separated from the culture before being used in the processes.

When cells or cell free extracts containing amidase produced by the method of the invention are heated to temperatures in the range 40° to 80° C. we have found that, most unusually, the amidase activity is irreversibly increased by 1.5 to 35 times dependent upon the enzyme preparation. This effect is greatest at temperatures in the range 55° to 65° C., especially in the range 58° to 62° C., at pHs in the range 4 to 9, especially at pHs between 6 and 7 and at protein concentrations in the range 0.1 to 200 mg/ml. Under these conditions little significant denaturation of amidase takes place.

Heating suitably takes place for a period in the range 20 minutes to 10 hours, especially 30 minutes to 180 minutes in some instances. To produce the increased activity the cells or cell-free enzyme can be heated immediately after they have been produced by the method of the invention or at some later time. The method of the invention can usefully be carried out either as described above or as a similar process having three steps, i.e. a first fermentation step in which cells having induced amidase are grown in a fermenter, a second heat shock step in which cells are subjected to heating to a temperature in the ranges described above and a third separation step in which a precipitate containing debris is separated from a supernatant liquid containing the enzyme.

The amidase enzyme the activity of which is increased by the method of the invention may be contained in whole microbial cells or in crude or purified extracts thereof. The enzyme may be derived from any suitable microbial source. Suitable bacterial sources include strains of the genera Brevibacterium, Pseudomonas, Alcaligenes, Arthobacter, Corynebacterium, Mycobacterium, Lactobacillus, Bacillus, Micrococcus, Nocardia and Streptomyces. Suitable yeasts and fungi include strains of Fusarium and Aspergillus.

Very suitable sources are strains of the species *Methylophilus methylotrophus* in which the enzyme has been induced as described in our co-pending British Patent Application No. 8630029 (ICI Case B 34138) by cultivation in a medium containing appropriate nutrients and an amide under conditions such that the enzyme is induced in the bacterium.

The species *Methylophilus methylotrophus* (formerly named *Pseudomonas methylotropha*), strains of which may be heated in the method of the invention, is described in our UK Patent Specification No. .1370892. Strains of this species suitable for use in the method of the invention have been deposited at the following 3 culture collections from which cultures are available:

1. The National Collection of Industrial Bacteria (NCIB), Torrey Research Station, PO Box 31, 135 Abbey Road, Aberdeen AB9 8DG, Scotland, UK;

2. The Agricultural Research Culture Collection (NRRL), 1815 North University Street, Peoria, Ill. 61604, U.S.A.; and 3. The Fermentation Research Institute (FRI), Agency of Industrial Science and Technology, Ministry of International Trade and Industry, 1 - 3 Higashi 1-Chome, Yatabe-machi, Tsukuba-gun, Ibaragi-ken, Japan.

The corresponding accession numbers assigned to the strains deposited at these collections are as follows:
NCIB 10508 - 10515 & 10592 - 10596, all inclusive;
NRRL B 5352 - B 5364 inclusive; and
FRI 1215 - 1227 inclusive.

A preferred strain in which amidase may be induced is *Methylophilus methylotrophus* strain AS-1 (NCIB 10515) which may safely be used in treating, e.g. polyacrylamide polymers intended for use in connection with foods. The species *Methylophilus methylotrophus* and the above strains, particularly strain AS-1, have become widely known and are mentioned in numerous publications both by us and others. In addition to the deposits mentioned above cultures of them are also held in a number of Universities and other laboratories in the UK and in other countries. Also very suitable for use in the method of the invention is strain NCIB 11585, available from NCIB, the production of which by the genetic modification of strain NCIB is described in our European Patent Specification 35831 B and a number of other publications.

| *Methylophilus methylotrophus* amidase properties | | | |
|---|---|---|---|
| Physiological status | Inducible | | |
| Location | Cytoplasmic | | |
| Protein | Soluble | | |
| | Acidic | Isoelectric point | 4.2 |
| | Tetrameric | | |
| | Native MW | (Gel permeation) | 155,000 |
| | Monomer MW | (SDS page) | 38,000 |
| Properties | pH optimum | Acetamide | 5 |
| | | Acrylamide | 8 |
| | Temperature optimum | | 60° C. |
| | Km | Acetamide | 0.2 mM |
| | | Acrylamide | 10 mM |
| | Activities | Acyl amidase | |
| | | Acyl transferase | |
| | Substrate | $C_1 < C_2 < C_3 > C_4 > C_5$ | |
| | | Acetamide < Acrylamide > propionamide | |

Amidase can be induced in *Methylophilus methylotrophus* when it is cultivated aerobically in a medium containing sources of carbon, nitrogen, phosphorus and other appropriate nutrients with an amide being present under conditions such that amidase is induced in the bacterial cells. Suitably cultivation takes place at a temperature in the range 20° to 40° C., preferably 34° to 38° C., and at a pH in the range 5.0 to 8.0, preferably 5.8 to 7.6. Cultivation can be by batch culture, single stage continuous culture or multiple stage continuous culture. A suitable dilution rate for continuous culture is in the range 0.05 $hr^{-1}$ to 0.55 $hr^{-1}$. Methanol is the preferred carbon source. Any suitable amide may be present in the culture medium. Acetamide or formamide are preferred. Other suitable amides include amides of carboxylic acids having the formula:

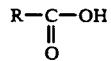

Where R is a short chain aliphatic group, i.e. containing 1 to 5 carbon atoms, which may be a straight or a branched chain. Preferably the amide is the sole or major nitrogen source and cultivation is by continuous culture under nitrogen limitation. A very suitable culture medium has the following composition:

| Component | Amount present/liter |
| --- | --- |
| Phosphoric acid | 1.6 ml |
| $MgSO_4.7H_2O$ | 1.912 g |
| $K_2SO_4$ | 0.952 g |
| $CuSO_4.5H_2O$ | 0.840 mg |
| $ZnSO_4.H_2O$ | 2.568 mg |
| $MnSO_4.4H_2O$ | 4.04 mg |
| $FeSO_4.7H_2O$ | 37.20 mg |
| Calcium formate | 0.173 g |

Nitrogen is supplied either from acetamide alone or from acetamide and ammonia. Cells are grown in nitrogen excess or nitrogen limitation at a range of cell concentrations.

Cells produced by continuous, batch or fed batch fermentation can be harvested by any suitable means preferably by ultrafiltration or centrifugation to produce a slurry having 10–25% by weight dry solids. Suitably this slurry is broken, e.g. by several freeze-thaw cycles or by mechanical breakage in a bead mill or french pressure device. Cell debris may then be removed by centrifugation leaving a crude cell-free extract containing amidase. Heat treatment may take place before or after this centrifugation but preferably before as this gives improved sedimentation of the product during centrifugation in addition to stimulating activity. This extract can if desired be further purified by anionic ion exchange chromatography and gel filtration. The cell free amidase preparations are suitably stored cool at 0° to 10° C. or as frozen solutions or as freeze dried preparations prior to hydration and use.

In the process of the invention amidase can be used to reduce free acrylamide residues occurring in all types of acrylamide polymers, particularly latices of the three basic chemical types. When treating a latex an amidase solution is added to the latex and is dispersed through the latex by stirring or similar mixing techniques at a level between 1 and 10,000 units/kg latex preferably 100–2000 U/kg latex. Incubation of amidase with the latex results in conversion of free acrylamide to acrylic acid or a salt thereof. Incubation temperatures of 10° C. to 100° C. (particularly 30° to 80° C.) are preferred. The latices are suitably treated over a pH range 3 to 10, preferably 5 to 7.

The amidase with increased activity produced in the method of the invention converts acrylamide into acrylic acid. This reaction can therefore be used as a means for producing acrylic acid or, when carried out in the presence of a suitable salt or alcohol, to produce salts or esters of acrylic acid.

The amidase when heated by the method of the invention above exhibits very high activity. This greatly extends the range of utility of polyacrylamide polymers.

The invention is illustrated by the following Examples:

EXAMPLE 1

Heat stimulation of the amidase activity of cell free extracts of Methylophilus methylotrophus AS-1.

A series of cell free extracts prepared from *Methylophilus methylotrophus* AS-1 in a citrate-phosphate buffer system at pH 6.0 and at a concentration of 30 mg protein per ml were heated in a water bath for periods of 1 and 2 hours at a series of temperatures between 30° and 70° C. Samples were withdrawn at various times and were assayed for amidase activity at 30° C. The substrate used in all cases was acrylamide at a concentration of 100 mM. The assays were performed at 30° C. in a 0.1M citrate: 0.2M phosphate buffer system at pH 6.0.

The results are shown in the Table and show increased activity under most of the conditions used with the highest increases being at 60° C. Increases were greater after 2 hours heating than after 1 hour.

TABLE

| Treatment | Amidase Activity (U/ml)* | Stimulation |
| --- | --- | --- |
| none | 3.69 | — |
| heating for 1 hr @ | | |
| 30° C. | 3.69 | 1 × |
| 50° C. | 5.91 | 1.6 × |
| 60° C. | 24.65 | 6.7 × |
| 70° C. | 14.68 | 3.9 × |
| heating for 2 hrs @ | | |
| 30° C. | 3.76 | 1.02 × |
| 50° C. | 8.86 | 2.04 × |
| 60° C. | 40.06 | 10.8 × |
| 70° C. | 2.28 | 0.62 × |

*1 unit is defined as 1 μmole of $NH_3$ released per minute.

EXAMPLE 2

Cell-free extracts as described in Example 1 were incubated at 55° C., 60° C. and 65° C. respectively. Samples were taken at various times and assayed for amidase activity as described in Example 1. The results are set out in FIG. 1 which is a graph of amidase activity (Units/ml) against activation time (mins) and show optimal stimulation of amidase activity at 60° C. over a period of two hours. Incubation at lower temperatures results in slower activation. Incubation at higher temperatures, e.g. at 65° C., shows an initial stimulation of rate of activation compared to 60° C. but a lower final amidase activity.

EXAMPLE 3

Removal of acrylamide from an anionic latex

An anionic latex, Nalfloc type A 626 produced by the Nalfloc Co. of Cheshire, UK, pH adjusted to 5.9 at 60° C. was treated by addition of an amidase solution produced by the method of the invention of 300 units per ml activity to a final level of 1000 units amidase per kg latex. Samples were withdrawn at 1 varying times and were analysed for free acrylamide by high pressure liquid chromatography (HPLC).

Figure 2:
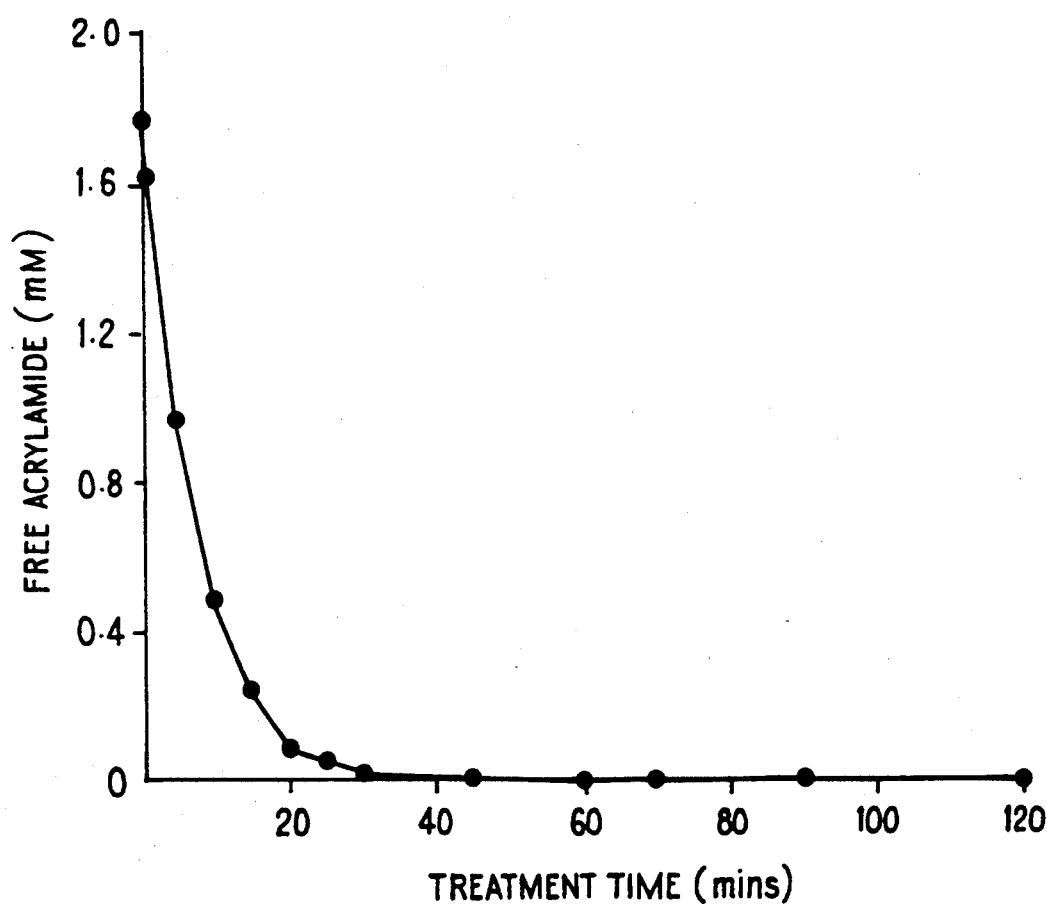

The results are set out in FIG. 2 which is a graph of free acrylamide (mM) against treatment time (mins) and show a reduction in free acrylamide level from 1.78 mM (126 ppm) to 0.02 mM (1.4 ppm) within 30 minutes.

EXAMPLE 4

Removal of acrylamide from a cationic latex.

A cationic latex, Nalfloc type 4625-SC, pH adjusted to 6.0 was treated as described in Example 3 with samples being analysed by HPLC.

Figure 3:
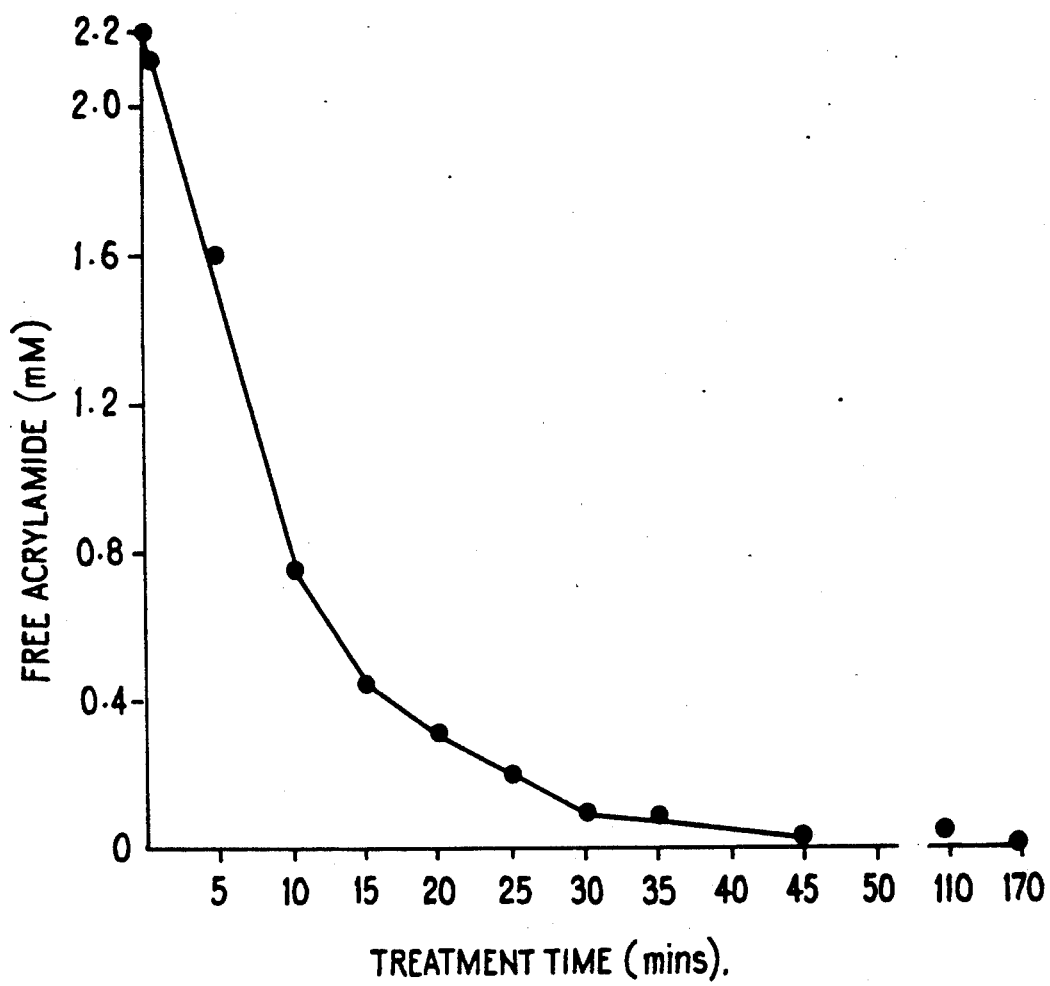

The results are set out in FIG. 3 which is a graph of free acrylamide (mM) against treatment time (mins) and show a reduction in free acrylamide level from 2.2 mM (156 ppm) to 0.02 mM (1.4 ppm) within 45 minutes.

EXAMPLE 5

Removal of acrylamide from a non-ionic latex.

A non-ionic latex, Nalfloc type 8861-SC pH adjusted to 6.0 was treated as described in Example 3 with samples being analysed by HPLC.

Figure 4:
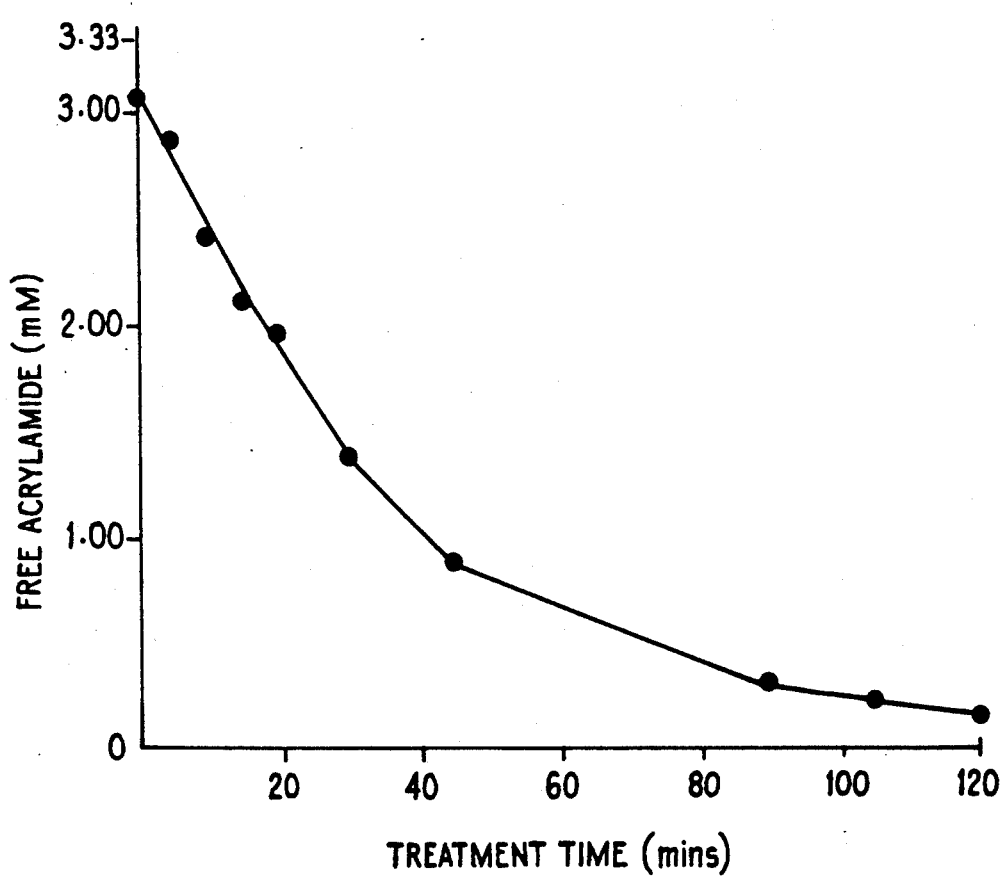

The results are set out in FIG. 4 which is a graph of free acrylamide (mM) against treatment time (mins) and show a reduction in free acrylamide level from 3.1 mM (220 ppm) to 0.15 mM (10.7 ppm) within 120 minutes.

EXAMPLE 6

A series of cell-free extracts prepared from *Methylophus methylotrophus* pH adjusted to pH 5, 6, 7 and 8 by buffer exchange through Pharmacia RD10 gel filtration columns was incubated at 60° C. at these pH's. Samples were taken for amidase activity analysis at various times at pH 6.0 as described in Example 1.

The results are set out in FIG. 5 which is a graph of amidase activity (units (U)/ml) against time of heating (mins) and show maximum stimulation of amidase at pH 7.0. Incubation at pH 5, 6 and 8 results in significantly less stimulation of activity.

EXAMPLE 7

A paste comprising whole and partially broken cells of *Methylophilus methylotrophus* produced according to the method of the invention and having a solids content of 10% was heated at 60° C. Samples were taken at various times for amidase activity analysis as described in Example 1.

The results are set out in FIG. 6 which is a graph of amidase activity in units (U) per mg dry cell weight (DCW) against heating time (hrs) and show maximum stimulation of activity after 7 hours increasing from 0.06 U/mg DCW to 1.25 U/mg DCW.

We claim:

1. A method for the production of an amidase enzyme of increased activity which comprises heating microbial cells of *Methylophilus methylotrophus* containing the enzyme, or extracts of said cells containing the enzyme, in the presence of an amide to a temperature in the range of 40° to 80° C. at a pH of 4 to 9 at a protein concentration in the range of 0.1 to 200 mg/ml and for a period of time in the range of 20 minutes to 10 hours whereby an increase in amidase activity for decomposing acrylamide is induced.

2. A method according to claim 1 wherein the cells or extracts containing the enzyme are heated to a temperature in the range of 55° to 65° C.

3. A method according to claim 2 wherein the cells or extracts containing the enzyme are heated to a temperature in the range of 58° to 62° C.

4. In a process for the decomposition of acrylamide in a medium containing it in which the medium is contacted with enzyme capable of decomposing the acrylamide under conditions suitable for the enzyme to decompose the acrylamide, the improvement wherein the enzyme utilized for the decomposition is an amidase enzyme obtained by heating microbial *Methylophilus methylotrophus*, or extracts of said cells containing the enzyme, in the presence of an amide to a temperature in the range of 40° to 80° C. at a pH of 4 to 9 at a protein concentration in the range of 0.1 to 200 mg/ml and for a period of time in the range of 20 minutes to 10 hours to increase the activity of the enzyme for decomposing acrylamide.

5. A process according to claim 4 wherein the enzyme is one which has been heated to a temperature in the range of 40° to 80° C. whilst it is contained in broken cells or is associated with cell debris.

6. In a process for the production of acrylic acid or a salt or ester thereof in which a medium containing acrylamide is contacted with an enzyme capable of decomposing acrylamide to acrylic acid under conditions suitable for the enzyme to decompose the acrylamide to acrylic acid or a salt or ester thereof, the improvement wherein the enzyme which is utilized is an amidase enzyme obtained by heating microbial cells of *Methylophilus methlotrophus*, or extracts of said cells containing the enzyme, in the presence of an amide to a temperature in the range of 40° to 80° C. at a pH of 4 to 9 at a protein concentration in the range of 0.1 to 200 mg/ml and for a period of time in the range of 20 minutes to 10 hours to increase the activity of the enzyme for decomposing acrylamide.

* * * * *